United States Patent [19]

Itoh et al.

[11] Patent Number: 4,528,287
[45] Date of Patent: Jul. 9, 1985

[54] 6-FLUORO-1, 4-DIHYDRO-4-OXO-7-SUBSTITUTED PIPERAZINYLQUINOLINE-3-CARBOXYLIC ACIDS AND THE METHOD FOR PREPARING THE SAME

[75] Inventors: Yasuo Itoh, Katsuyamashi; Hideo Kato, Fukuishi; Nobuo Ogawa; Eiichi Koshinaka, both of Katsuyamashi; Tomio Suzuki, Kamishiimura; Noriyuki Yagi, Katsuyamashi, all of Japan

[73] Assignee: Hokuriku Pharmaceutical Co., Ltd., Katsuyamashi, Japan

[21] Appl. No.: 651,423

[22] Filed: Sep. 17, 1984

[30] Foreign Application Priority Data

Sep. 19, 1983 [JP] Japan .................. 58-171271
Mar. 12, 1984 [JP] Japan .................. 59-45664
Jun. 18, 1984 [JP] Japan .................. 59-123780

[51] Int. Cl.³ .................. A61K 31/47; C07D 401/04
[52] U.S. Cl. .................. 514/254; 544/363
[58] Field of Search .................. 544/353, 250

[56] References Cited

U.S. PATENT DOCUMENTS 4,146,719  3/1979  Irikura .................. 544/363
4,292,317  9/1981  Pesson .................. 544/363
4,398,029  8/1983  Irikura et al. .................. 544/363

FOREIGN PATENT DOCUMENTS 2939786  4/1980  Fed. Rep. of Germany ...... 544/363
3106013  9/1982  Fed. Rep. of Germany ...... 544/363
59-10580  1/1984  Japan .................. 544/363
59-29685  2/1984  Japan .................. 544/363
2085875A  5/1982  United Kingdom .................. 544/363

Primary Examiner—Glennon H. Hollrah
Assistant Examiner—James H. Turnipseed
Attorney, Agent, or Firm—Gordon W. Hueschen

[57] ABSTRACT

The invention is concerned with the novel piperazinyl-quinoline-3-carboxylic acids represented by formula (I)

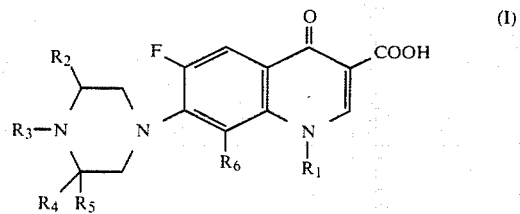

or a pharmacologically-acceptable salt thereof, a process for the preparation of them, and a pharmaceutical composition which contains these new compounds as active ingredient and can be used as the therapeutic agent against bacteria.

10 Claims, No Drawings

6-FLUORO-1, 4-DIHYDRO-4-OXO-7-SUBSTITUTED PIPERAZINYLQUINOLINE-3-CARBOXYLIC ACIDS AND THE METHOD FOR PREPARING THE SAME

BACKGROUND OF THE INVENTION

1. Field of the Invention

The present invention relates to novel 6-fluoro-1,4-dihydro-4-oxo-7-substituted piperazinylquinoline-3-carboxylic acids which have an excellent antibacterial effect, its pharmacologically-acceptable salts, and process for preparing the same.

More particularly, the present invention relates to novel 6-fluoro-1,4-dihydro-4-oxo-7-substituted piperazinylquinoline-3-carboxylic acids represented by the general formula (I),

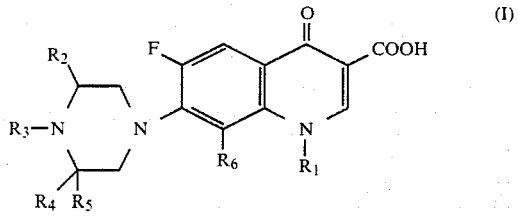

wherein $R_1$ is a lower alkyl group having 1 to 4 carbon atoms, a vinyl group, a 2-fluoroethyl group, or a 2-hydroxyethyl group; $R_2$, $R_3$ and $R_4$ each is a hydrogen, or a lower alkyl group having each 1 to 4 carbon atoms; $R_5$ is a lower alkyl group having 1 to 4 carbon atoms and $R_6$ is a hydrogen, or a fluorine atom, its pharmacologically acceptable salt and process for preparing the same.

FIELD OF THE INVENTION

So far, as antibacterial medicines, those of pyridone carboxylic acids have been widely used. For example, nalidixic acid, piromidic acid, pipemidic acid, and cinoxacine have been marketed for the clinical treatment of urinary tract infection, intestinal infection and cholangia infection. The most effective and widely used antibacterial among these is pipemidic acid (The Merck Index, 10th Edition, 7332) represented by the following formula (II):

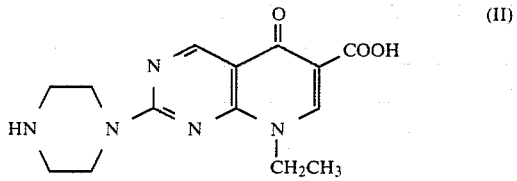

Recently, norfloxacin (The Merck Index, 10th Edition, 6541) was synthesized to improve the antibacterial effect of pipemidic acid and to expand its antibacterial spectrum. It has the chemical formula (III) as shown below and used for the clinical treatment of infectious impetigo, phlegmon, subcutaneous abscess, or tonsillitis.

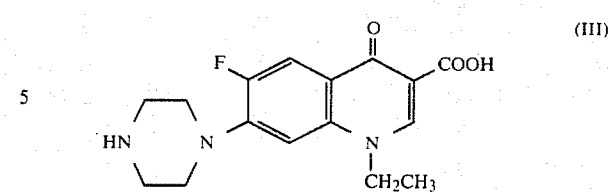

However, such marketed antibacterials were unsatisfactory as they had to be applied in large quantities so that their continuous and long-term administration could cause adverse side-effects, for example, gastrointestinal function disorder.

SUMMARY OF THE INVENTION

The present inventors studied therefore for finding out a more effective antibacterial, and discovered that the compounds represented by the above-mentioned general formula (I) are more effective as an antibacterial when compared with pipemidic acid (II) and norfloxacin (III) and excellent in their rate of urinary excretion as well as in their low toxicity.

The present invention is based on this finding.

DETAILED DESCRIPTION OF THE INVENTION

In this invention the lower alkyl group represented by $R_1$-$R_5$ in the general formula (I) includes, for example, methyl, ethyl, propyl, isopropyl, butyl, isobutyl, and tertbutyl, especially methyl, and ethyl.

Pharmacologically-acceptable salts of the compound having the said general formula (I) are acid addition salts or alkali addition salts. The former includes mineral acid salts such as hydrochloride, sulfate, nitrate, hydrobromide, hydroiodide, phosphate, etc.; or organic acid salts such as acetate, maleate, fumarate, citrate, or tartarate, etc. The latter includes inorganic alkali salts such as sodium, potassium, calcium, or ammonium salt, etc.; or organic base salts such as ethanolamine salt, or N,N-dialkyl ethanolamine salt, etc.

Non-limiting examples of the compounds of this invention include.

(1) 1-Ethyl-6,8-difluoro-1,4-dihydro-7-(3-methyl-1-piperazinyl)-4-oxoquinoline-3-carboxylic acid.

(2) 1-Ethyl-6,8-difluoro-1,4-dihydro-7-(3-methyl-1-piperazinyl)-4-oxoquinoline-3-carboxylic acid hydrochloride.

(3) 1-Ethyl-6-fluoro-1,4-dihydro-7-(3-methyl-1-piperazinyl)-4-oxoquinoline-3-carboxylic acid hydrochloride.

(4) 6-Fluoro-1-(2-fluoroethyl)-1,4-dihydro-7-(3-methyl-1-piperazinyl)-4-oxoquinoline-3-carboxylic acid.

(5) 6,8-Difluoro-1-(2-fluoroethyl)-1,4-dihydro-7-(3-methyl-1-piperazinyl)-4-oxoquinoline-3-carboxylic acid.

(6) 6,8-Difluoro-1,4-dihydro-7-(3-methyl-1-piperazinyl)-4-oxo-1-vinylquinoline-3-carboxylic acid.

(7) 6,8-Difluoro-1,4-dihydro-1-methyl-7-(3-methyl-1-piperazinyl)-4-oxoquinoline-3-carboxylic acid.

According to the present invention the novel compounds, 6-fluoro-1,4-dihydro-4-oxo-7-substituted piperazinylquinoline-3-carboxylic acids, represented by the general formula (I) can be prepared by various methods.

In a first method, the compound having the said formula (I) is obtained by reacting a 6-fluoro-7-halogeno-1,4-dihydro-4-oxoquinoline-3-carboxylic acid, having the following general formula (IV),

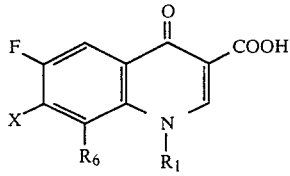

wherein $R_1$ and $R_6$ each has the same meaning as that described above, while X is chlorine, or fluorine, with a piperazine represented by the following general formula (V),

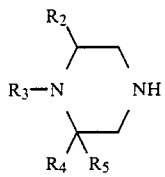

wherein $R_2$, $R_3$, $R_4$ and $R_5$ each has the same meaning as described above, in the presence, or absence of a solvent.

The solvent used in the process is, for example, water, alcohols such as butanol, 3-methoxy butanol, or isoamyl alcohol; ethers such as ethylene glycol dimethyl ether (monoglyme), diethylene glycol dimethyl ether (diglyme), triethylene glycol dimethyl ether (triglyme); aprotic polar solvents such as dimethyl formamide, dimethyl sulfoxide, or hexamethyl phosphoric triamide; aromatic hydrocarbons such as benzene or toluene; or organic bases such as pyridine, picoline, lutidine, collidine, or triethylamine.

The above mentioned reaction is to be carried out within the temperature range from room temperature to 200° C., preferably from 100° to 180° C.

The starting material of this method, a 6-fluoro-7-halogeno-1,4-dihydro-4-oxoquinoline-3-carboxylic acid having the general formula (IV), is, for instance, those already disclosed in Japanese Patent Publication (unexamined) No. 141286/1978, Japanese Patent Publication (unexamined) No. 47658/1980 and Japanese Patent Publication (unexamined) No. 30964/1981.

The piperazines having the general formula (V) are also a known substance and disclosed in, for example, U.S. Pat. No. 2,780,625 and South Africa Pat. No. 6,807,552.

In a second method, the inventive compound represented by the general formula (I) is prepared by hydrolyzing a 6-fluoro-1,4-dihydro-4-oxo-7-substituted piperazinylquinoline-3-carboxylic acid ester derivative represented by the following general formula (VI),

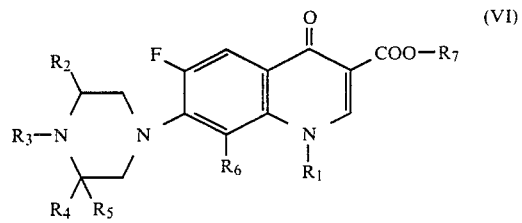

wherein $R_1$, $R_2$, $R_3$, $R_4$, $R_5$ and $R_6$ each has the same meaning as described above and $R_7$ is s lower alkyl group having 1 through 4 carbon atoms.

The hydrolysis is carried out according to the known method using an acid such as hydrochloric acid, or sulfuric acid; or an alkali such as sodium hydroxide, or potassium hydroxide.

These acids or alkalis can be used for the hydrolysis in the form of aqueous solutions, ethanol or methanol solutions, or solutions of aqueous organic solvents.

The reaction is to be carried out at a temperature within the range from room temperature to the reflux temperature of the solvent.

The starting materials of the said method, 6-fluoro-1,4-dihydro-4-oxo-7-substituted piperazinylquinoline-3-carboxylic acid esters are novel substances, and a method for their preparation is described in the following examples for reference.

In a third method of this invention, the compounds represented by the general formula (I) are prepared by using a 6-fluoro-1,4-dihydro-4-oxo-7-substituted piperazinylquinoline-3-carboxylic acid having the following general formula (VII),

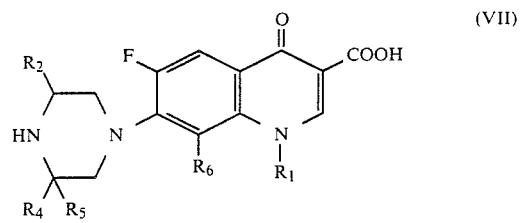

wherein $R_1$, $R_2$, $R_4$, $R_5$ and $R_6$ each has the same meaning as descrived above. This formula is the same as the said formula (I) except that $R_3$ is replaced with a hydrogen atom. The above compound is reacted with a carbonyl compound represented by the following general formula (VIII),

wherein $R_8$ is a hydrogen atom, or a lower alkyl group having 1 through 3 carbon atoms, in the presence of formic acid.

Examples of the carbonyl compound having the general formula (VIII) are formaldehyde, acetaldehyde and propionaldehyde. Formaldehyde is used preferably in the form of its aqueous solution (formalin). In case of acetaldehyde, or propionaldehyde, it is desirable to use nitrobenzene as a solvent for the reaction.

The reaction is carried out at a temperature within the range of 100 to 200 C., preferably at the reflux temperature of the reaction solvent.

In a fourth method of the present invention, the compound represented by the general formula (I) is prepared by reacting a 6-fluoro-1,4-dihydro-4-oxo-7-substituted piperazinylquinoline-3-carboxylic acid having the general formula (VII) with an alkyl halogenide represented by the general formula (IX).

$$R_3-A \qquad (IX)$$

wherein $R_3$ has the same meaning as that described above and A is a halogen, in a solvent in the presence or absence of a base as a deoxidizing agent.

The solvent of this reaction can be of any kind so far as it does not inhibit the reaction. The examples are acetone, ethanol, ether, tetrahydrofuran, dimethylformamide, dioxane, benzene, toluene, or chloroform.

A deoxidizing agent that can be used in the present invention is, for example, triethylamine, pyridine, or potassium carbonate.

The reaction is carried out at a temperature within the range from room temperature to the reflux temperature of the solvent, preferably at 50° to 100° C.

The novel compounds, 6-fluoro-1,4-dihydro-4-oxo-7-substituted piperazinylquinoline-3-carboxylic acids represented by the general formula (I) and their pharmacologically-acceptable salts, which are obtained according to the methods described so far, have an antibacterial effect against both gram-positive and gram-negative microorganisms and are very useful as medicines.

The effect of antimicrobiological activity, antibacterial spectrum and urinary excretion are shown in Tables 1 and 2 respectively as examples illustrating the potentiating pharmacological effect of the compounds.

The acute toxicity has been determined as shown in Table 3, whereby as a reference drug, norfloxacin, market product represented by formula (III), is used.

TEST COMPOUNDS

Compound of Invention (Example 1)

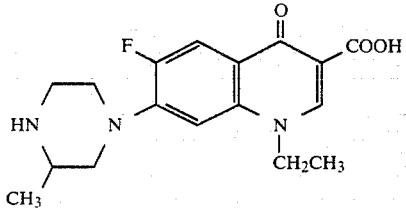

Compound of Invention (Example 4)

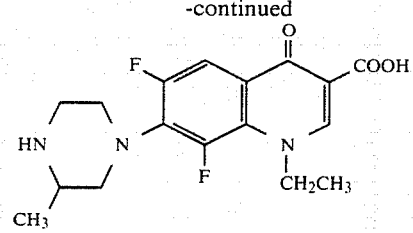

Compound of Invention (Example 16)

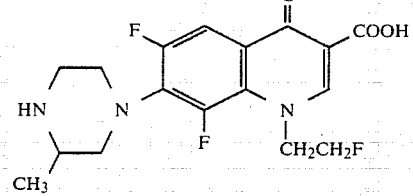

Compound of Invention (Example 20)

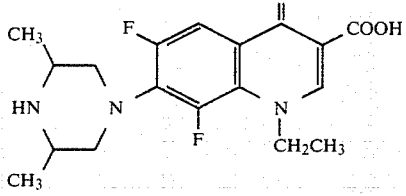

Reference Drug (norfloxacin)

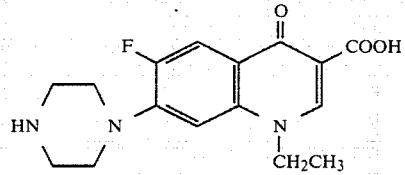

1. ANTIBACTERIAL SPECTRUM

Experiment

Minimum inhibitory concentrations (MIC) were determined by the twofold agar dilution method (Chemotherapy, 29(1), 76(1981)). Overnight cultures in Mueller-Hinton broth were suspended by buffered saline gelatine. One loopful of the bacterial suspension ($10^6$ or $10^8$ colony-forming units/ml) was incubated onto the test compound-containing plates. The plates were incubated for 18 hrs. at 37° C. The MIC was the lowest concentration of the drug that inhibited visible growth. The results are shown in Table 1.

TABLE 1

Antibacterial Spectrum (Minimum concentration causing growth inhibition, μg/ml. $10^6$ cells/ml)

| Bacteria | Gram | Example 1 | Example 4 | Example 16 | Example 20 | Ref. Drug |
|---|---|---|---|---|---|---|
| *Bacillus subtilis* ATCC6633 | + | 0.10 | 0.10 | 0.20 | 0.20 | 0.10 |
| *Micrococcus luteus* ATCC9341 | + | 25 | 6.25 | 6.25 | 12.5 | 6.25 |
| *Staphylococcus aureus* FAD208PJC-1 | + | 0.20 | 0.38 | 0.38 | 0.78 | 0.20 |
| *Staphylococcus aureus* Terajima | + | 0.39 | 0.78 | 0.78 | 1.56 | 0.39 |
| *Staphylococcus aureus* MS-353 | + | 0.39 | 0.78 | 1.56 | 1.56 | 6.25 |
| *Streptococcus pyogenes* Cook | + | 3.13 | 3.13 | 3.13 | 6.25 | 1.56 |
| *Escherichia coli* NIHJ-JC-2 | − | 0.10 | 0.05 | 0.10 | 0.39 | 0.05 |
| *Escherichia coli* K-12 C600 | − | 0.10 | 0.05 | 0.20 | 0.20 | 0.05 |
| *Klebsiella pneumoniae* PCI-602 | − | 0.025 | 0.0125 | 0.023 | 0.20 | 0.025 |
| *Salmonella typhimurium* IID 971 | − | 0.10 | 0.05 | 0.20 | 0.20 | 0.05 |
| *Salmonella typhi* 901 | − | 0.05 | 0.0125 | 0.10 | 0.10 | 0.025 |
| *Salmonella paratyphi* 1015 | − | 0.0125 | 0.025 | 0.05 | 0.10 | 0.025 |

TABLE 1-continued

| | Antibacterial Spectrum (Minimum concentration causing growth inhibition, μg/ml. $10^6$ cells/ml) | | | | | |
|---|---|---|---|---|---|---|
| Bacteria | Gram | Example 1 | Example 4 | Example 16 | Example 20 | Ref. Drug |
| *Salmonella schottmulleri* 0006 | — | 0.025 | 0.025 | 0.10 | 0.10 | 0.025 |
| *Salmonella enteritidis* G14 | — | 0.10 | 0.05 | 0.20 | 0.39 | 0.05 |
| *Serratia marcescens* IAM1184 | — | 0.20 | 0.10 | 0.20 | 0.78 | 0.10 |
| *Pseudomonas aeruginosa* ATCC9027 | — | 0.10 | 0.05 | 0.10 | 0.20 | 0.05 |
| *Pseudomonas aeruginosa* IFO3445 | — | 0.78 | 0.78 | 0.78 | 3.13 | 0.78 |
| *Pseudomonas aeruginosa* NCTC10490 | — | 0.39 | 0.78 | 0.38 | 0.78 | 0.78 |
| *Pseudomonas aeruginosa* PAO7 | — | 0.78 | 1.56 | 1.56 | 3.13 | 0.39 |
| *Proteus morganii* IFO3848 | — | 0.025 | 0.025 | 0.05 | 0.20 | 0.025 |
| *Proteus mirabilis* IFO3849 | — | 0.39 | 0.20 | 0.39 | 1.56 | 0.10 |
| *Proteus vulgalis* OX-19 | — | 0.05 | 0.05 | 0.20 | 0.10 | 0.05 |
| *Proteus vulgalis* HX-19 | — | 0.025 | 0.025 | 0.05 | 0.20 | 0.025 |
| *Proteus rettgeri* IFO3850 | — | 0.10 | 0.05 | 0.20 | 0.39 | 0.05 |
| *Enterobacter aerogenes* ATCC13048 | — | 0.10 | 0.10 | 0.20 | 0.20 | 0.10 |
| *Enterobacter cloaceas* 963 | — | 0.10 | 0.10 | 0.20 | 0.20 | 0.05 |

*free

2. URINARY EXCRETION

Experiment

Male rats of SD strain, weighing 180–210 g, were used 8 animals at a group. Test compounds suspended in 0.5% carboxymethyl cellulose were administered per os to 24 hr-fasted rats at dose of 20 mg/Kg. Urine was pooled from 0 to 6 hrs. and 6 to 24 hrs, and urinary excretion was measured by bioassay using *Escherichia coli* NIHJ-JC-2. The results are shown in Table 2.

Bioassay

The assay method employed was the cup-plate method using *Escherichia coli* NIHJ-JC-2. Urine was appropriately diluted with 1/15M phosphate buffer pH7.0, before assay if necessary. Standard calibration lines were made in 1/15M phosphate buffer pH7.0.

TABLE 2

| | Urinary Excretion | | |
|---|---|---|---|
| | Drug Concentration in Urine (μg/ml) | | Rate of Urinary Excretion (%) |
| Drug | 0–6 | 6–24 (hr) | 0–24 (hr) |
| Example 1 | 514 | 28 | 30 |
| Example 4* | 659 | 87 | 75 *free |
| Example 16 | 344 | 46 | 41 |
| Reference Drug | 63 | 9 | 10 |

3. ACUTE TOXICITY

Experiment

Male mice of ddY strain, 4 weeks old, were used with 10 animals at a group. Test compounds suspended in 0.5% carboxymethyl cellulose were administered per os (p.o.) in mice. In the case of intraveneous (i.v.) administration, test compounds were solved in 0.1N-HCl solution and neutralized with 0.1N-NaOH solution. $LD_{50}$ was determined by the Probit method from dead animals at the end of 10 days. The results are shown in Table 3.

TABLE 3

| | Acute Toxicity | |
|---|---|---|
| | $LD_{50}$ (mg/kg) | |
| Drug | p.o. | i.v. |
| Example 1 | >4000 | 348.5(326.6–372.0)*[1] |
| Example 4*[2] | >4000 | 245.6(223.7–269.6) |
| Reference Drug | >4000 | 229.5(211.1–252.7) |

*[1] ( ) = 95% Confidence Limit
*[2] free

It is clearly seen from the results above that the compounds of this invention exhibit a potent effect on urinary excretion and excellent lower toxicity as compared to the reference drug.

Further, the antibacterial spectrum shows that the compounds of the invention exhibit approximately equal to the reference drug.

Therefore, it is clear that the compounds of the invention are very useful as a medicine for clinical usage because of the superior pharmaceutical effects, as excellent absorption, and of the lower toxicity.

Thus, the present compound is much safer than traditionally marketed medicine and considered to be highly useful as a clinical medicine.

Necessary amount for treatment: Normally, a total of 150–1000 mg is to be orally administered by dividing the amount into 2–4 times per day per adult.

This preparation of the compound of the invention is further explained hereinbelow with the examples, which are given by way of illustration and not to be considered as limiting.

EXAMPLE 1

1-Ethyl-6-fluoro-1,4-dihydro-7-(3-methyl-1-piperazinyl)-4-oxoquinoline-3-carboxylic acid A mixture of 15.00 g of 7-chloro-1-ethyl-6-fluoro-1,4-dihydro-4-oxoquinoline-3-carboxylic acid, 16.70 g of 2-methylpiperazine and 70 ml of pyridine was heated for 14 hours under reflux. The solvent of the reaction mixture was evaporated and the residue was acidified with 50% aqueous acetic acid. The solution was treated with activated carbon and neutralized with 20% aqueous sodium hydroxide. Then, the solution was treated with activated carbon again, and concentrated. The precipitate was filtered and dissolved in ethanol. The solution was acidified with ethanolic hydrogen chloride and concentrated. The precipitate was filtered and recrystallized from aqueous ethanol to give 8.19 g of hydrochloride of the title compound as pale yellow needles, M.p. >300° C.

Analysis for $C_{17}H_{20}FN_3O_3 \cdot HCl$: Calculated %: C, 55.21; H, 5.72; N, 11.36; Found %: C, 55.13; H, 5.72; N, 11.17.

EXAMPLE 2

7-(3,4-Dimethyl-1-piperazinyl)-1-ethyl-6-fluoro-1,4-dihydro-4-oxoquinoline-3-carboxylic acid A mixture of 2.69 g of 1-ethyl-6-fluoro-1,4-dihydro-7-(3-methyl-1-piperazinyl)-4-oxoquinoline-3-carboxylic acid hydrochloride, 5.4 ml 90% formic acid, 3.5 ml of 37% formalin and 0.70 g of potassium carbonate was heated for 5 hours under reflux. The reaction mixture was neutralized with 20% aqueous sodium hydroxide. The precipitate was filtered and recrystallized from a mixture of chloroform and methanol to give 1.70 g of the title compound as colorless needles, M.p. 244°–246° C.

Analysis for $C_{18}H_{22}FN_3O_3$: Calculated %: C, 62.24; H, 6.38; N, 12.10; Found %: C, 62.02; H, 6.37; N, 12.05.

EXAMPLE 3

1-Ethyl-7-(4-ethyl-3-methyl-1-piperazinyl)-6-fluoro-1,4-dihydro-4-oxoquinoline-3-carboxylic acid A solution of 1.00 g of 1-ethyl-6-fluoro-1,4-dihydro-7-(3-methyl-1-piperazinyl)-4-oxoquinoline-3-carboxylic acid hydrochloride, 1.29 g of ethyl iodide and 1.09 g of triethylamine in 20 ml of N,N-dimethylformamide was heated at 70° to 80° C. for 1.5 hours. The solvent of the reaction mixture was evaporated and the residue was acidified with 50% aqueous acetic acid. The solution was neutralized with 20% aqueous sodium hydroxide and the precipitate was filtered. The precipitate was chromatographed on silica gel using chloroform-methanol (9:1) as eluent to give 0.47 g of the title compound as colorless crystalls, which was recrystallized from a mixture of chloroform and methanol as colorless needles, M.p. 203°–205° C.

Analysis for $C_{19}H_{24}FN_3O_3$: Calculated %: C, 63.14; H, 6.69; N, 11.63; Found %: C, 62.82; H, 6.78; N, 11.66.

EXAMPLE 4

1-Ethyl-6,8-difluoro-1,4-dihydro-7-(3-methyl-1-piperazinyl)-4-oxoquinoline-3-carboxylic acid A mixture of 1.00 g of 1-ethyl-6,7,8-trifluoro-1,4-dihydro-4-oxoquinoline-3-carboxylic acid, 1.10 g of 2-methylpiperazine and 10 ml of pyridine was heated for 15 minutes under reflux. The reaction mixture was evaporated and methanol was added to the residue. The precipitate was filtered and recrystallized from ethanol to give 0.36 g of the title compound as colorless needles, M.p. 239°–240.5° C.

Analysis for $C_{17}H_{19}F_2N_3O_3$ Calculated %: C, 58.11; H, 5.45; N, 11.96 Found %: C, 57.98; H, 5.47; N, 12.18.

By the usual manner the hydrochloride was prepared and recrystallized from water as colorless needles, M.p. 290°–300° C. (decomp.).

Analysis for $C_{17}H_{19}F_2N_3O_3 \cdot HCl$: Calculated %: C, 52.65; H, 5.20; N, 10.84; Found %: C, 52.78; H, 5.32; N, 10.65.

EXAMPLE 5

7-(3,4-Dimethyl-1-piperazinyl)-1-ethyl-6,8-difluoro-1,4-dihydro-4-oxoquinoline-3-carboxlic acid A mixture of 1.40 g of 1-ethyl-6,8-difluoro-1,4-dihydro-7-(3-methyl-1-piperazinyl)-4-oxoquinoline-3-carboxylic acid, 2.8 ml of 90% formic acid and 2.2 ml of 37% formalin was heated for 4 hours under reflux. The reaction mixture was evaporated and the residue was dissolved in water. The solution was neutralized with aqueous sodium bicarbonate. The precipitate was filtered and recrystallized from ethanol to give 0.32 g of the title compound as colorless needles, M.p. 211.5°–212° C.

Analysis for $C_{18}H_{21}F_2N_3O_3$: Calculated %: C, 59.17; H, 5.79; N, 11.50; Found %: C, 59.29; H, 5.87; N, 11.55.

EXAMPLE 6

1-Ethyl-6,8-difluoro-1,4-dihydro-7-(3-methyl-1-piperazinyl)-4-oxoquinoline-3-carboxylic acid (a) To a solution of 0.55 g of ethyl 1-ethyl-6,8-difluoro-1,4-dihydro-7-(3-methyl-1-piperazinyl)-4-oxoquinoline-3-carboxylate in 5.5 ml of ethanol 11 ml of 18% hydrochloric acid was added and the mixture was heated for 4 hours under reflux. The precipitate was filtered and washed with ethanol and ether. Recrystallization from water gave 0.43 g of hydrochloride of the title compound as colorless needles. This compound was identical with NMR and IR spectra of that prepared in example 4.

(b) Ethyl 1-ethyl-6,8-difluoro-1,4-dihydro-7-(3-methyl-1-piperazinyl)-4-oxoquinoline-3-carboxylate used above was prepared as follows.

A mixture of 1.50 g of ethyl 1-ethyl-6,7,8-trifluoro-1,4-dihydro-4-oxoquinoline-3-carboxylate, 1.50 g of 2-methylpiperazine and 5 ml of pyridine was heated for 3 hours under reflux. The solvent of the reaction mixture was evaporated and the residue was dissolved in chloroform. The solution was washed with water, dried and evaporated. The residue was recrystallized from a mixture of benzene and isopropyl ether to give 1.00 g of the title compound as colorless needles, M.p. 126.5°–127.5° C.

Analysis for $C_{19}H_{23}F_2N_3O_3$: Calculated %: C, 60.15; H, 6.11; N, 11.08; Found %: C, 60.30; H, 6.34; N, 10.84.

EXAMPLE 7

6,8-Difluoro-1,4-dihydro-1-isopropyl-7-(3-methyl-1-piperazinyl)-4-oxoquinoline-3-carboxylic acid (a) A mixture of 0.68 g of 6,7,8-trifluoro-1,4-dihydro-1-isopropyl-4-oxoquinoline-3-carboxylic acid, 0.72 g of 2-methyl piperazine and 10 ml of pyridine was treated in the same manner as described for Example 4 to give 0.42 g of the title compound as colorless crystals. M.p. 217°–218° C.

Analysis for $C_{18}H_{21}F_2N_3O_3 \cdot \frac{1}{2}H_2O$: Calculated %: C, 57.75; H, 5.92; N, 11.22; Found %: C, 57.53; H, 5.97; N, 11.13.

(b) 6,7,8-Trifluoro-1,4-dihydro-1-isopropyl-4-oxoquinoline-3-carboxylic acid used above was prepared as follows.

7.70 g of sodium borohydride was added to a mixture of 3.70 g of 2,3,4-trifluoroaniline, 10.30 g of sodium acetate, 20 ml of acetone, 19.6 ml of acetic acid and 39 ml of water under stirring and ice-cooling. After 2 hours, the reaction mixture was made alkaline with sodium carbonate and extracted with benzene. The extract was washed with NaCl saturated water, dried and the solvent was evaporated to give 3.17 g of 2,3,4-trifluoro-N-isopropyl aniline as colorless oil.

IR $_{max}^{film} \nu$ cm$^{-1}$: 3450 (NH)

A mixture of 2.50 g of 2,3,4-trifluoro-N-isopropylaniline and 2.80 g of diethyl 2-ethoxymethylenemalonate was heated for 1 hour at 160-170 C. Hexane was added to the reation mixture and then cooled. The crystals were filtered to give 2.45 g of diethyl 2-(2,3,4-trifluoro-N-isopropylanilino)methylene malonate, which was recrystallized from hexane as colorless needles, M.p. 92.5°-93° C.

Analysis for $C_{17}H_{20}F_3NO_4$: Calculated %: C, 56.82; H, 5.61; N, 3.90; Found%: C, 56.83; H, 5.67; N, 3.91.

A mixture of 9.00 g of diethyl 2-(2,3,4-trifluoro-N-isopropylanilino)methylenemalonate and 90.0 g of poly phosphoric acid was heated for 1 hour at 80°-85° C. under stirring. The reaction mixture was poured to ice-water and extracted with chloroform. The extract was washed with water, dried and the solvent was evaporated. A mixture of 90 ml of 18% hydrochloric acid and 45 ml of ethanol was added to the residue and refluxed for 1.5 hours.

The precipitate was filtered and washed with ethanol to give 1.40 g of the title compound, which was recrystallized from a mixture of chloroform and ethanol as pale brown needles, M.p. 261°-262.5° C.

Analysis for $C_{13}H_{10}F_3NO_3$: Calculated %: C, 54.74; H, 3.53; N, 4.91; Found %: C, 54.64; H, 3.47; N, 4.93.

EXAMPLE 8

(R)-(+)-1-Ethyl-6,8-difluoro-1,4-dihdro-7-(3-methyl-1-piperazinyl)-4-oxoquinoline-3-carboxlic acid A mixture of 2.00 g of 1-ethyl-6,7,8-trifluoro-1,4-dihydro-4-oxoquinoline-3-carboxylic acid, 1.50 g of (R)-(−)-2-methylpiperazine($[\alpha]_D^{21°}$ −6.4° (c=1, ethanol)) and 15 ml of pyridine was heated for 15 minutes under reflux. After completion of the reaction, the solvent was evaporated and the residue was dissolved in 10% hydrochloric acid. The solution was neutralized with aqueous sodium bicarbonate. The precipitate was filtered, dried and dissolved in a mixture of chloroform and methanol. The solution was acidified with ethanolic hydrogen chloride. The precipitate was filtered and dissolved in water. The solution was neutralized with aqueous sodium bicarbonate and the precipitate was filtered to give 1.72 g of the title compound, which was recrystallized from a mixture of chloroform and ethanol as colorless needles, M.p. 244.5°-245.5° C., $[\alpha]_D^{21°}$ +39.5° (c=1, chloroform).

Analysis for $C_{17}H_{19}F_2N_3O_3$: Calculated %: C, 58.11; H, 5.45; N, 11.96; Found%: C, 58.12; H, 5.72; N, 12.07.

EXAMPLE 9

6-Fluoro-1-(2-fluoroethyl)-1,4-dihydro-7-(3-methyl-1-piperazinyl)-4-oxoquinoline-3-carboxylic acid A mixture of 1.50 g of 7-chloro-6-fluoro-1-(2-fluoroethyl)-1,4-dihydro-4-oxoquinoline-3-carboxylic acid, 1.60 g of 2-methylpiperazine and 8 ml of pyridine was heated for 11 hours under reflux. The solvent of the reaction mixture was evaporated and the residue was dissolved in hot water. After cooling of the solution, the precipitate was filtered and recrystallized from ethanol to give 0.62 g of the title compound as colorless needles, M.p. 226°-227° C.

Analysis for $C_{17}H_{19}F_2N_3O_3$: Calculated %: C, 58.11; H, 5.45; N, 11.96; Found %: C, 58.14; H, 5.80; N, 11.61.

In same manner as described in the Examples 1 to 9, the compounds of the Examples 10 to 29 below were prepared.

TABLE 4

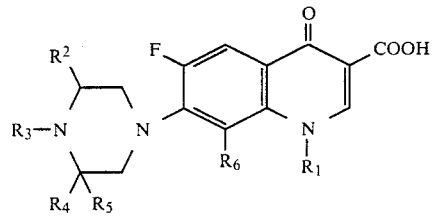

| Example No. | $R_1$ | $R_2$ | $R_3$ | $R_4$ | $R_5$ | $R_6$ | Crystal | m.p. (solvent) |
|---|---|---|---|---|---|---|---|---|
| 10*[1] | Et | H | H | H | Et | H | colorless crystalls | >300° ($H_2O$—acetone) |
| 11 | Et | H | Me | H | Et | H | colorless needles | 213–215° ($CHCl_3$—MeOH) |
| 12*[1] | Me | H | H | H | Me | H | colorless needles | >300° ($H_2O$—EtOH) |
| 13 | Me | H | H | H | Me | F | colorless scales | 249–250° ($CHCl_3$—EtOH) |
| 14*[2] | Et | H | H | H | Me | F | colorless needles | 242.5–243.5° ($CHCl_3$—EtOH) |
| 15 | —CH=$CH_2$ | H | H | H | Me | F | pale yellow crystalls | 254–255° (decompn.) ($H_2O$) |
| 16 | —$(CH_2)_2$F | H | H | H | Me | F | colorless needles | 262–163° ($CHCl_3$—EtOH) |
| 17*[1] | —$(CH_2)_2$OH | H | H | H | Me | H | colorless needles | 295–298° (decompn.) ($H_2O$—EtOH) |
| 18 | —$(CH_2)_2$OH | H | Me | H | Me | H | colorless needles | 258–260° (decompn.) ($CHCl_3$—MeOH) |
| 19*[1] | Et | Me | H | H | Me | H | colorless crystalls | >300° (MeOH) |
| 20 | Et | Me | H | H | Me | F | colorless crystalls | 233–234° ($CHCl_3$—EtOH) |
| 21 | Et | H | H | Me | Me | H | colorless crystalls | 208.5–209.5° (EtOH) |
| 22 | Et | H | H | Me | Me | F | pale yellow needles | 207–208° (EtOH) |
| 23 | Et | Me | Me | H | Me | F | colorless needles | 216–217° (EtOH) |
| 24 | Me | H | Me | H | Me | H | colorless needles | 262–263° ($CH_2Cl_2$—EtOH) |
| 25 | Pr | H | H | H | Me | H | pale yellow crystalls | 163–164° (EtOH—$C_6H_6$) |
| 26 | Pr | H | Me | H | Me | H | pale yellow needles | 157–158° ($C_6H_6$—hexane) |
| 27 | iPr | H | Me | H | Me | F | pale yellow needles | 190.5–191.5° ($C_6H_6$—hexane) |
| 28 | Pr | H | H | H | Me | F | pale yellow needles | 211–212° ($CHCl_3$—EtOH) |
| 29 | Pr | H | Me | H | Me | F | pale yellow scales | 186.5–187.5° (EtOH) |

| | Analysis | | | | | | |
|---|---|---|---|---|---|---|---|
| | | Calculated | | | Found | | |
| Example No. | Formula | C: | H: | N: | C: | H: | N: |
| 10*[1] | $C_{18}H_{22}FN_3O_3 \cdot HCl$ | 56.32 | 6.04 | 10.95 | 56.10 | 6.01 | 10.89 |
| 11 | $C_{19}H_{24}FN_3O_3$ | 63.14 | 6.69 | 11.63 | 63.11 | 7.01 | 11.54 |
| 12*[1] | $C_{16}H_{18}FN_3O_3 \cdot HCl \cdot \tfrac{1}{4}H_2O$ | 53.34 | 5.45 | 11.66 | 53.31 | 5.75 | 11.56 |

TABLE 4-continued

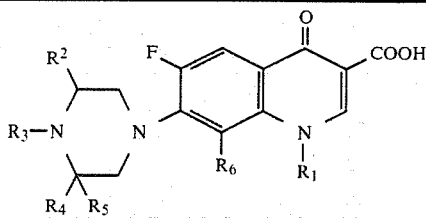

| | | | | | | | |
|---|---|---|---|---|---|---|---|
| 13 | $C_{16}H_{17}F_2N_3O_3$ | 56.98 | 5.08 | 12.46 | 56.86 | 5.36 | 12.17 |
| 14*[2] | $C_{17}H_{19}F_2N_3O_3$ | 58.11 | 5.45 | 11.96 | 58.01 | 5.64 | 11.77 |
| 15 | $C_{17}H_{17}F_2N_3O_3\cdot\frac{1}{2}H_2O$ | 56.98 | 5.06 | 11.73 | 57.04 | 5.18 | 11.46 |
| 16 | $C_{17}H_{18}F_3N_3O_3$ | 55.28 | 4.91 | 11.38 | 55.10 | 5.02 | 11.41 |
| 17*[1] | $C_{17}H_{20}FN_3O_4\cdot HCl$ | 52.92 | 5.49 | 10.89 | 52.57 | 5.72 | 10.72 |
| 18 | $C_{18}H_{22}FN_3O_4$ | 59.40 | 6.10 | 11.56 | 59.14 | 6.39 | 11.49 |
| 19*[1] | $C_{18}H_{22}FN_3O_3\cdot HCl$ | 56.32 | 6.04 | 10.95 | 56.05 | 6.27 | 10.84 |
| 20 | $C_{18}H_{21}F_2N_3O_3$ | 59.17 | 5.79 | 11.50 | 59.23 | 5.95 | 11.49 |
| 21 | $C_{18}H_{22}FN_3O_3$ | 62.23 | 6.38 | 12.10 | 62.10 | 6.62 | 11.86 |
| 22 | — | — | — | — | — | — | — |
| 23 | $C_{19}H_{23}F_2N_3O_3$ | 60.15 | 6.11 | 11.08 | 60.09 | 6.49 | 11.09 |
| 24 | $C_{17}H_{20}FN_3O_3$ | 61.25 | 6.05 | 12.60 | 60.94 | 6.38 | 12.51 |
| 25 | $C_{18}H_{22}FN_3O_3\cdot\frac{1}{2}H_2O$ | 61.43 | 6.44 | 11.94 | 61.20 | 6.58 | 11.73 |
| 26 | $C_{19}H_{24}FN_3O_3$ | 63.14 | 6.69 | 11.63 | 62.98 | 6.98 | 11.61 |
| 27 | $C_{19}H_{23}F_2N_3O_3$ | 60.15 | 6.11 | 11.08 | 60.00 | 6.35 | 11.13 |
| 28 | $H_{18}H_{21}F_2N_3O_3$ | 59.17 | 5.79 | 11.50 | 58.86 | 6.14 | 11.38 |
| 29 | $H_{19}H_{23}F_2N_3O_3$ | 60.15 | 6.11 | 11.08 | 59.85 | 6.31 | 10.92 |

*[1]hydrochloride
*[2](S)—(−)−,$[\alpha]_n^{20}$-34.1° (C = 1, CHCl$_3$)

EXAMPLE 30

7-(3,4-Dimethyl-1-piperazinyl)-6,8-dihydro-1,4-dihydro-1-methyl-4-oxoquinoline-3-carboxylic acid A mixture of 700 mg of 6,7,8-trfluoro-1,4-dihydro-1-methyl-4-oxoquinoline-3-carboxylic acid, 930 mg of 1,2-dimethylpiperazine and 5 ml of pyridine was heated for 20 minutes under reflux. The reaction mixture was evaporated and the residue was dissolved in a mixture of chloroform and methanol. The solution was acidified with ethanolic hydrogen chloride. Then the precipitate was filtered and dissolved in water. The solution was neutralized with sodium bicarbonate and extracted with chloroform. The extract was washed with water, dried and evaporated. Methanol was added to the residue and the precipitate was filtered to give 730 mg of the desired compound, which was recrystallized from a mixture of chloroform and ethanol as colorless needles, M.p. 231°–232.5° C.

Analysis for $C_{17}H_{19}F_2N_3O_3$: Calculated %: C, 58.11; H, 5.45; N, 11.96; Found %: C, 58.13; H, 5.54; N, 11.99.

Thereafter, the following compounds are given in same manner as described for Example 30.

EXAMPLE 31

7-(3,4-Dimethyl-1-piperazinyl)-6,8-difluoro-1,4-dihydro-4-oxo-1-vinylquinoline-3-carboxylic acid yellow needles, M.p. 178°–179° C. (EtOH)
Analysis for $C_{18}H_{19}F_2N_3O_3$: Calculated %: C,59.50; H, 5.27; N, 11.56; Found %: C, 59.20; H, 5.57; N, 11.58.

EXAMPLE 32

7-(3,4-Dimethyl-1-piperazinyl)-6-fluoro-1-(2-fluoroethyl)-1,4-oxoquinoline-3-carboxylic acid pale yellow needles, M.p. 238.5°–239.5° C. (CHCl$_3$-EtOH)
Analysis for $C_{18}H_{21}F_2N_3O_3$: Calculated %: C, 59.17; H, 5.79; N, 11.50; Found %: C, 58.99; H, 5.97; N, 11.49.

EXAMPLE 33

7-(3,4-Dimethyl-1-piperazinyl)-6,8-difluoro-1-(2-fluoroethyl)-1,4-dihydro-4-oxoquinoline-3-carboxylic acid colorless scales, M.p. 224.5°–225° C. (CHCl$_3$-EtOH)
Analysis for $C_{18}H_{20}F_3N_3O_3$: Calculated %: C, 56.39; H, 5.26; N, 10.96; Found %: C, 56.41; H, 5.38; N, 10.98.

What is claim is:

1. A 6-fluoro-1,4-dihydro-4-oxo-7-substituted piperazinyl-quinoline-3-carboxylic acids represented by the general formula (I)

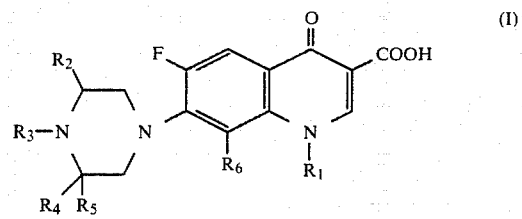

wherein $R_1$ is a lower alkyl group having 1 to 4 carbon atoms, a vinyl group, a 2-fluoroethyl group, or a 2-hydroxy-ethyl group; $R_2$, $R_3$ and $R_4$ each is a hydrogen, or a lower alkyl group having 1 to 4 carbon atoms; $R_5$ is a lower alkyl group having 1 to 4 carbon atoms and $R_6$ is a hydrogen, or a fluorine and a pharmacologically-acceptable salt thereof.

2. Compound of claim 1 which is 1-Ethyl-6,8-difluoro-1,4-dihydro-7-(3-methyl-1-piprazinyl)-4-oxoquinoline-3-carboxylic acid.

3. Compound of claim 1 which is 1-Ethyl-6,8-difluoro-1,4-dihydro-7-(3-methyl-1-piperazinyl)-4-oxoquinoline-3-carboxylic acid hydrochloride.

4. Compound of claim 1 which is 1-Ethyl-6-fluoro-1,4-dihydro-7-(3-methyl-1-piperazinyl)-4-oxoquinoline-3-carboxylic acid hydrochloride.

5. Compound of claim 1 which is 6-Fluoro-1-(2-fluoroethyl)-1,4-dihydro-7-(3-methyl-1-piperazinyl)-4-oxoquinoline-3-carboxylic acid.

6. Compound of claim 1 which is 6,8-Difluoro-1-(2-fluoroethyl)-1,4-dihydro-7-(3-methyl-1-piperazinyl)-4-oxoquinoline-3-carboxylic acid.

7. Compound of claim 1 which is 6,8-Difluoro-1,4-dihydro-7-(3-methyl-1-piperazinyl)-4-oxo-1-vinylquinoline-3-carboxylic acid.

8. Compound of claim 1 which is 6,8-Difluoro-1,4-dihydro-1-methyl-7-(3-methyl-1-piperazinyl)-4-oxoquinoline-3-carboxylic acid.

9. Pharmaceutical compositions useful for the inhibition of bacteria and for increased urinary excretion comprising an effective antibacterial amount of one or more compounds as claimed in claim 1 together with a pharmaceutically-acceptable carrier.

10. Method for the inhibition of bacteria and for increasing urinary excretion in a subject in need of the same, comprising the step of administering an effective antibacterial and urinary-excretion increasing amount of a compound of claim 1 orally to said patient.

* * * * *

UNITED STATES PATENT AND TRADEMARK OFFICE
CERTIFICATE OF CORRECTION

PATENT NO. : 4,528,287

DATED : July 9, 1985

INVENTOR(S) : Yasuo Itoh, Hideo Kato, Nobuo Ogawa, Eiichi Koshinaka Tomio Suzuki and Noriyuki Yagi It is certified that error appears in the above-identified patent and that said Letters Patent is hereby corrected as shown below:

Title page, [73] Assignee:, line 2; "Katsuyamashi" should read -- Fukui --
Col. 6, Table 1, first column, line 3; "FAD208PJC-1" should read
-- FAD209PJC-1 --
Col. 6, Table 1, fourth column, line 3; "0.38" should read -- 0.39 --
Col. 7, Table 1-continued, column 1, line 1; "0006" should read -- 8006 --
Col. 7, Table 1-continued, column 1, line 14 (last line); "cloaceas"
should read -- cloaceae --
Col. 12, Table 4, 8th column, lines 1, 6, 10, 11, 12 and 16, in each
instance change "crystalls" to -- crystals --
Col. 13, line 34; "-trfluoro-" should read -- -trifluoro- --
Col. 14, line 35; "What is claim is" should read -- What is claimed is --

Col. 6, line 5 of Table 1; "4" should read -- 4* --
Col. 7, line 5 of Table 1-continued; "4" should read -- 4* --
Col. 7, last line of Table 1-continued; "*free" should read -- *free acid --
Col. 7, line 46;"*free" should read -- *free acid --
Col. 9, line 65; "-carboxlic" should read -- -carboxylic --

Signed and Sealed this

Fifteenth Day of April 1986

[SEAL]

Attest:

DONALD J. QUIGG

Attesting Officer

Commissioner of Patents and Trademarks

UNITED STATES PATENT AND TRADEMARK OFFICE

CERTIFICATE EXTENDING PATENT TERM
UNDER 35 U.S.C. § 156

PATENT NO.:       4,528,287

DATED:            July 9, 1985

INVENTORS:        Yasuo Itoh et al.

PATENT OWNER:     Hokuriku Pharmaceutical Co., Ltd.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,030 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks